US009192817B2

(12) United States Patent
Frolov

(10) Patent No.: US 9,192,817 B2
(45) Date of Patent: Nov. 24, 2015

(54) DEVICE FOR TRAINING SWIMMERS AND PERFORMING PHYSIOTHERAPEUTIC EXERCISES

(71) Applicant: Anthony Frolov, Bell Canyon, CA (US)

(72) Inventor: Anthony Frolov, Bell Canyon, CA (US)

( * ) Notice: Subject to any disclaimer, the term of this patent is extended or adjusted under 35 U.S.C. 154(b) by 0 days.

(21) Appl. No.: 14/108,530

(22) Filed: Dec. 17, 2013

(65) Prior Publication Data

US 2014/0171270 A1    Jun. 19, 2014

Related U.S. Application Data

(60) Provisional application No. 61/738,004, filed on Dec. 17, 2012.

(51) Int. Cl.
*A63B 31/00*    (2006.01)
*A63B 71/00*    (2006.01)
(Continued)

(52) U.S. Cl.
CPC ............ *A63B 35/00* (2013.01); *A61H 33/6005* (2013.01); *A63B 69/0059* (2013.01);
(Continued)

(58) Field of Classification Search
CPC ............... A63B 2244/20; A63B 35/00; A63B 69/0059; A63B 69/12; A63B 2225/15; A63B 2213/005; A63B 69/125; A63B 2230/207; A63B 2225/72; A63B 2230/30; A63B 2220/13; A63B 2230/06; A63B 2230/42; A63B 2220/17; A63B 2225/107; A63B 2225/50; A63B 2220/833; A63B 2220/20; A63B 2220/51; A63B 2230/75; A63B 2220/30; A63B 2225/20; A61H 33/6005; A61H 2201/102; A61H 2201/5048; A61H 33/02; A61H 2201/5012; A61H 2201/1261; E04H 4/0031; G09B 19/0038; A61M 2021/0066; A61M 2205/3375; A61M 2205/3553; A61M 2230/205; A61M 2205/3584; A61M 2021/005; A61M 2205/332; A61M 21/0094; A61M 2205/52; A61M 2205/3368; A61M 2205/3561; A61M 2205/3592; A61M 2205/6018; A61M 2202/0208; A61M 2202/0291; A61M 2230/30; A61M 2021/0027; A61M 2205/505; A61M 2230/60; A61M 2021/0022; A61M 2205/75; A61M 2230/63; A61M 2230/42; A61M 2230/06; A61M 2021/0016; Y10T 29/49947; A62B 31/00
USPC ......... 482/8–9, 55; 434/254; 4/494, 488, 493, 4/498, 904
See application file for complete search history.

(56) References Cited

U.S. PATENT DOCUMENTS 3,559,215 A * 2/1971 Kormann .................. E04H 4/08
                                                    4/493
4,218,056 A * 8/1980 Whitling ........................ 482/55

(Continued)

FOREIGN PATENT DOCUMENTS

GB      2214800 A  *  9/1989  ............. A63B 31/00
GB      2316326 A  *  2/1998  ............. A63B 69/12

(Continued)

*Primary Examiner* — Oren Ginsberg
*Assistant Examiner* — Joshua Lee
(74) *Attorney, Agent, or Firm* — Georgiy L. Khayet

(57) ABSTRACT

Provided are a device for training swimmers and performing physiotherapeutic exercises, a method for assembling a device for training swimmers and performing physiotherapeutic exercises, a unit for measuring parameters of a swimmer, and a method for assembling a unit for measuring parameters of a swimmer. The device for training swimmers and performing physiotherapeutic exercises comprises a tank configured to accommodate a swimmer and a cover connected to the tank. The device for training swimmers and performing physiotherapeutic exercises further comprises a restraining element. A first end of the restraining element is connected to the tank and the second end of the restraining element is configured to be connected to the swimmer. The unit for measuring parameters of a swimmer comprises a housing, within which a motive force sensor, a processing unit, and a transmitter are enclosed.

24 Claims, 10 Drawing Sheets

(51) Int. Cl.
*E04H 4/00* (2006.01)
*A63B 69/12* (2006.01)
*A63B 35/00* (2006.01)
*A63B 69/00* (2006.01)
*G09B 19/00* (2006.01)
*A61H 33/00* (2006.01)
*A61H 33/02* (2006.01)
*A61M 21/00* (2006.01)

(52) U.S. Cl.
CPC .............. *A63B69/12* (2013.01); *E04H 4/0031* (2013.01); *G09B 19/0038* (2013.01); *A61H 33/02* (2013.01); *A61H 2201/102* (2013.01); *A61H 2201/1261* (2013.01); *A61H 2201/5012* (2013.01); *A61H 2201/5048* (2013.01); *A61M 21/0094* (2013.01); *A61M 2021/005* (2013.01); *A61M 2021/0016* (2013.01); *A61M 2021/0022* (2013.01); *A61M 2021/0027* (2013.01); *A61M 2021/0066* (2013.01); *A61M 2202/0208* (2013.01); *A61M 2202/0291* (2013.01); *A61M 2205/332* (2013.01); *A61M 2205/3368* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/6018* (2013.01); *A61M 2205/75* (2013.01); *A61M 2230/06* (2013.01); *A61M 2230/205* (2013.01); *A61M 2230/30* (2013.01); *A61M 2230/42* (2013.01); *A61M 2230/60* (2013.01); *A61M 2230/63* (2013.01); *A63B 69/125* (2013.01); *A63B 2213/005* (2013.01); *A63B 2220/13* (2013.01); *A63B 2220/17* (2013.01); *A63B 2220/20* (2013.01); *A63B 2220/30* (2013.01); *A63B 2220/51* (2013.01); *A63B 2220/833* (2013.01); *A63B 2225/107* (2013.01); *A63B 2225/15* (2013.01); *A63B 2225/20* (2013.01); *A63B 2225/50* (2013.01); *A63B 2225/72* (2013.01); *A63B 2230/06* (2013.01); *A63B 2230/207* (2013.01); *A63B 2230/30* (2013.01); *A63B 2230/42* (2013.01); *A63B 2230/75* (2013.01); *Y10T 29/49947* (2015.01)

(56) References Cited

U.S. PATENT DOCUMENTS

| | | | | |
|---|---|---|---|---|
| 4,527,795 A * | 7/1985 | Zink | ................. | 482/55 |
| 4,577,859 A * | 3/1986 | Gossett | ................. | 482/55 |
| 4,603,859 A * | 8/1986 | Schnaitl | ................. | 482/130 |
| 5,271,106 A * | 12/1993 | McClish et al. | ................. | 4/494 |
| 5,379,467 A * | 1/1995 | Lochbaum | ................. | 4/489 |
| 5,391,080 A * | 2/1995 | Bernacki et al. | ................. | 434/254 |
| 5,606,831 A * | 3/1997 | Tippmann | ................. | E04H 4/0043 220/678 |
| 5,846,167 A * | 12/1998 | Liu et al. | ................. | 482/55 |
| 5,938,565 A * | 8/1999 | Bernacki | ................. | 482/5 |
| 7,442,151 B1 * | 10/2008 | Berdegue | ................. | 482/55 |
| 8,572,769 B2 * | 11/2013 | Gamracy et al. | ................. | 4/545 |
| 2003/0189484 A1 * | 10/2003 | Rust et al. | ................. | 340/323 R |
| 2004/0086838 A1 * | 5/2004 | Dinis | ................. | 434/247 |
| 2005/0159275 A1 * | 7/2005 | Bullman et al. | ................. | 482/111 |
| 2008/0066758 A1 * | 3/2008 | Richardson | ................. | A61G 10/026 128/205.26 |
| 2010/0199969 A1 * | 8/2010 | Chan | ................. | E04H 3/16 126/561 |
| 2010/0269251 A1 * | 10/2010 | DeMotts | ................. | 4/492 |
| 2012/0017364 A1 * | 1/2012 | Mayaud | ................. | 4/494 |

FOREIGN PATENT DOCUMENTS

| | | | | |
|---|---|---|---|---|
| GB | 2422559 A * | 8/2006 | ............ | A63B 69/12 |
| WO | WO 0112123 A1 * | 2/2001 | | |
| WO | WO 2004012827 A1 * | 2/2004 | ............ | A63B 69/12 |

\* cited by examiner

DEVICE FOR TRAINING SWIMMERS AND PERFORMING PHYSIOTHERAPEUTIC EXERCISES

CROSS-REFERENCE TO RELATED APPLICATIONS

This patent application claims the priority benefit of U.S. provisional patent application No. 61/738,004, filed Dec. 17, 2012, the disclosure of which is incorporated by reference.

TECHNICAL FIELD

The application relates generally to training and physiotherapy devices and, more specifically, to devices for training swimmers, performing physiotherapeutic exercises, and learning to swim, and units for measuring parameters of swimmers.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

One of the approaches for treating spinal disorders involves straightening the vertebral column supported by spinal muscles. It is a well-established fact that swimming provides for rehabilitation with few contraindications of persons having spinal disorders. Swimming is also an optimal training exercise for people of any age. These are some of the reasons why pools are very popular.

When teaching persons to swim, training swimmers, or performing physiotherapeutic exercises with persons having spinal injuries or disorders, it is important to create pool conditions that allow the swimmer to feel comfortable. Traditional pools intended for simultaneous training of several persons do not allow adjusting the conditions in the pool to the needs and preferences of each person.

Furthermore, it is important to register the physical parameters of the person during swimming. Such parameters may be used for selecting a swimming or therapeutic program for the swimmer. Traditional pools do not allow monitoring the swimmer and registering physical parameters of the swimmer during physical activity in the pool.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

The present disclosure is related to approaches for training swimmers, performing physiotherapeutic exercises, learning to swim, and measuring parameters of a swimmer. Specifically, according to one approach of the present disclosure, a device for training swimmers and performing physiotherapeutic exercises is provided. The device for training swimmers and performing physiotherapeutic exercises comprises a tank configured to accommodate a swimmer and a cover connected to the tank. The device for training swimmers and performing physiotherapeutic exercises further comprises a restraining element. A first end of the restraining element is connected to the tank or the cover and the second end of the restraining element is configured to be connected to the swimmer.

According to another approach of the present disclosure, there is provided a unit for measuring parameters of a swimmer. The unit for measuring parameters of a swimmer comprises a housing, within which a motive force sensor, a processing unit, and a transmitter are enclosed. The motive force sensor is configured to measure a motive force associated with the swimmer. The processing unit is configured to process measurements received from the motive force sensor. The transmitter is configured to transmit the processed measurements to a peripheral unit. Fasteners are connected to the housing and configured to fasten a restraining element that transfers the motive force from the swimmer to the motive force sensor.

In further exemplary embodiments, modules, subsystems, or devices can be adapted to perform the recited steps. Other features and exemplary embodiments are described below.

BRIEF DESCRIPTION OF DRAWINGS

Embodiments are illustrated by way of example and not limitation in the figures of the accompanying drawings, in which like references indicate similar elements and in which.

DETAILED DESCRIPTION

Figure 1:
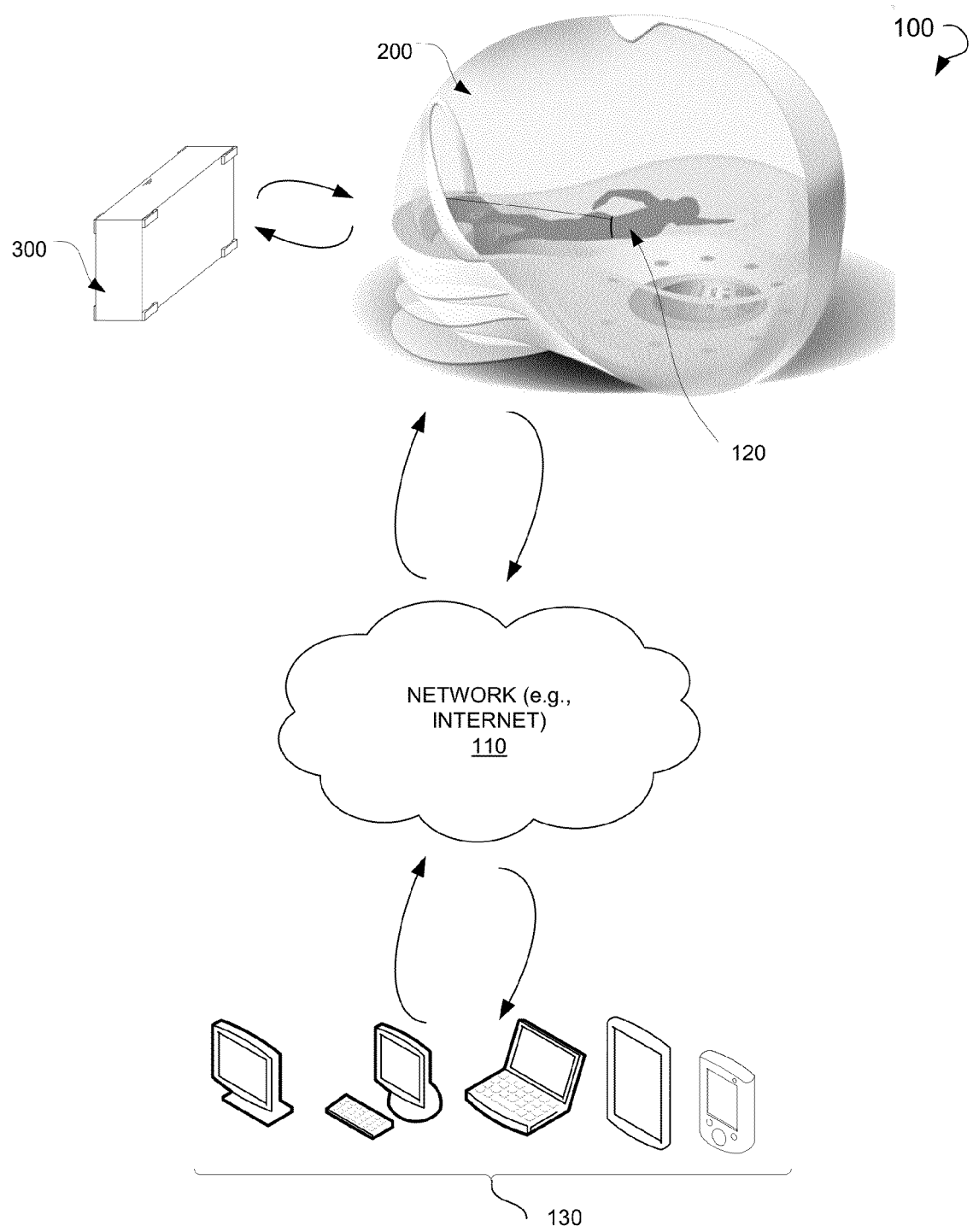
FIG. 1 illustrates an environment within which a device for training swimmers and performing physiotherapeutic exercises, a method for assembling a device for training swimmers and performing physiotherapeutic exercises, a unit for measuring parameters of a swimmer, and a method for assembling a unit for measuring parameters of a swimmer can be implemented.

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is therefore not to be taken in a limiting sense, and the scope is defined by the appended claims and their equivalents. In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated.

The present disclosure relates to a device for training swimmers, performing physiotherapeutic exercises, and learning to swim suitable for performing physiotherapeutic exercises for persons having orthopedic injuries or disorders. The orthopedic injuries or disorders may include spinal curvature, herniation of intervertebral disk, post-surgical rehabilitation, and so forth.

The compact size of the device for learning to swim, training swimmers, and performing physiotherapeutic exercises allows locating the device in relatively small premises. The device for learning to swim, training swimmers, and performing physiotherapeutic exercises may be disposed at any location, such as in hospitals, in schools, in swimming training centers, in gym locations, in office buildings, in rehabilitation centers, and even at home.

The device for training swimmers and performing physiotherapeutic exercises comprises a tank and a cover. The size of the tank is sufficient to accommodate a swimmer. The cover is configured to close the tank so as specific air and water conditions can be set inside the device for training swimmers and performing physiotherapeutic exercises. The device for training swimmers and performing physiotherapeutic exercises further comprises a regulating unit for controlling conditions inside the device. Therefore, the conditions inside the device for training swimmers and performing physiotherapeutic exercises are monitored and can be adjusted according to preferences of the swimmer or medical indications prescribed for the swimmer by a doctor. The device for training swimmers and performing physiotherapeutic exercises further comprises a display unit. The display unit may be located inside the device for training swimmers and performing physiotherapeutic exercises so that the swimmer can see the display unit during swimming. The display unit may show current parameters of the swimmer, visualization of movements of the swimmer, a swimming style, and so forth.

The present disclosure relates also to a unit for measuring parameters of the swimmer that can be a part of the device for training swimmers and performing physiotherapeutic exercises. The unit for measuring parameters of the swimmer is located on any side of the device for training swimmers and performing physiotherapeutic exercises. The characteristics measured by the unit for measuring parameters of the swimmer include pulse, blood pressure of the swimmer, speed of the swimmer, distance, intensity of movement of the swimmer, and the like. The unit for measuring parameters of the swimmer may be attached to the device for training swimmers and performing physiotherapeutic exercises permanently or using fixing elements.

The device for training swimmers and performing physiotherapeutic exercises further comprises a restraining element. The restraining element includes a tether, a rope, a resilient member or non-resilient member, and the like. A first end of the restraining element is connected, e.g., using a harness, to the swimmer. The second end of the restraining element is connected to the unit for measuring parameters of the swimmer. Thus, the restraining element transfers the motive force from the swimmer to the unit for measuring parameters of the swimmer. The unit for measuring parameters of the swimmer calculates characteristics of the swimmer on the basis of the tensile force acting on the restraining element.

The device for training swimmers and performing physiotherapeutic exercises further comprises a communication unit configured to set swimming modes for the swimmer. The swimming modes are selected based on the measurements collected by the unit for measuring parameters of the swimmer. Furthermore, the swimmer can select a swimming mode according to the preferences of the swimmer.

Referring now to the drawings, FIG. 1 shows an environment 100 within which a device for training swimmers and performing physiotherapeutic exercises, a method for assembling a device for training swimmers and performing physiotherapeutic exercises, a unit for measuring parameters of a swimmer, and a method for assembling a unit for measuring parameters of a swimmer can be implemented. The environment 100 may include a network 110, a device 200 for training swimmers and performing physiotherapeutic exercises, a unit 300 for measuring parameters of a swimmer, a swimmer 120, and one or more peripheral units 130.

The network 110 may include the Internet or any other network capable of communicating data between devices. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking. The network 110 may include a network of data processing nodes that are interconnected for the purpose of data communication. The network 110 may include a Software-defined Networking (SDN). The SDN may include one or more of the above network types. Generally, the network 110 may include a number of similar or dissimilar devices connected together by a transport medium enabling communication between the devices by using a predefined protocol. Those skilled in the art will recognize that the present disclosure may be practiced within a variety of network configuration environments and on a variety of computing devices.

The unit 300 for measuring parameters of a swimmer is connected to the device 200. The connection may be permanent or use fixing elements. The swimmer 120 is located inside the device 200 and connected to the unit 300 for measuring parameters of a swimmer. The unit 300 for measuring parameters of a swimmer collects and processes the parameters of the swimmer 120. The swimmer 120 represents a person in need of swimming training, learning to swim, performing physiotherapeutic exercises, and so forth. The unit 300 for measuring parameters of a swimmer transmits the processed parameters of the swimmer 120 to the peripheral unit 130. The peripheral unit 130 includes a mobile telephone, a personal computer (PC), a tablet PC, a laptop, a smartphone, a monitor, any personal digital device of the swimmer or any digital device in a location of the device 200 for training swimmers and performing physiotherapeutic exercises, and so forth.

Figure 2A:
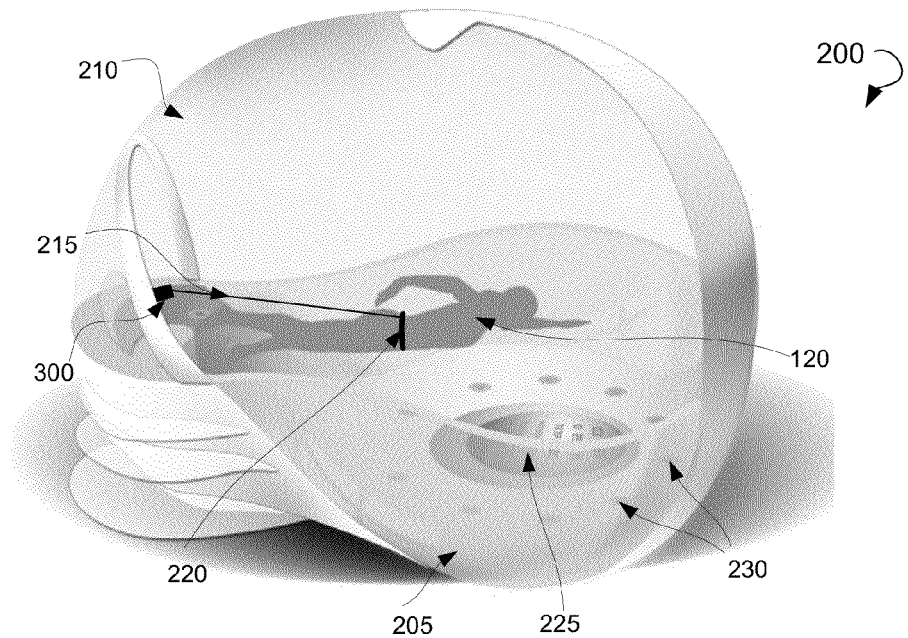
FIG. 2A shows a simplified perspective view of a device for training swimmers and performing physiotherapeutic exercises, in accordance with an example embodiment.

FIG. 2A shows a simplified perspective view of the device 200 for training swimmers and performing physiotherapeutic exercises. The device 200 comprises a tank 205 configured to accommodate a swimmer 120. The tank 205 may have sufficient dimensions so as to allow the swimmer 120 to execute normal swimming strokes. The tank 205 may be of any shape, such as round, rectangular, square, pear-shaped, and so forth. The tank 205 may be made of any material. In some embodiments, the tank 205 is transparent or partially transparent.

Figure 2B:
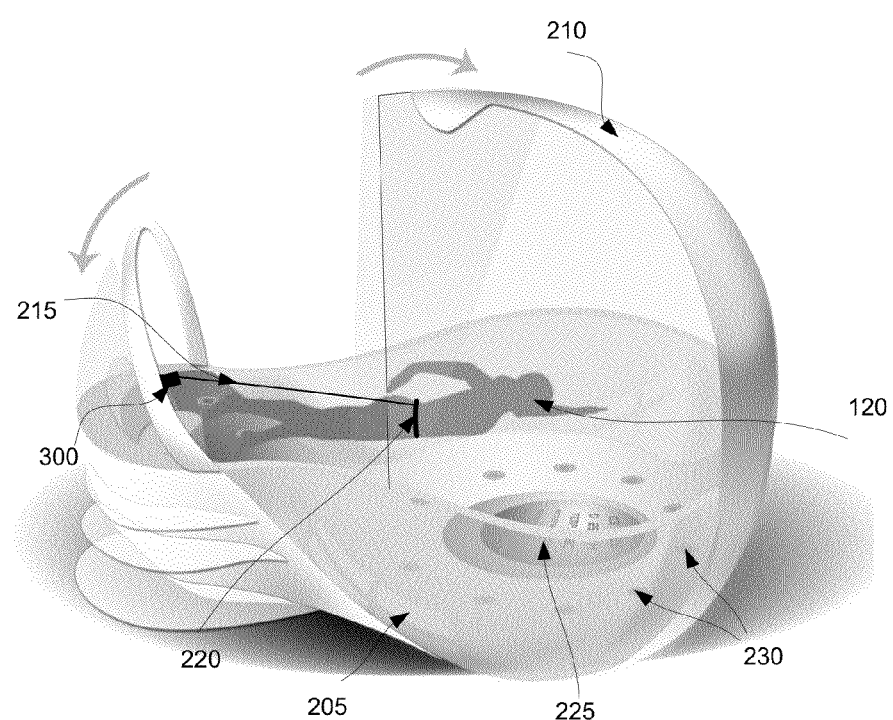
FIG. 2B shows a simplified perspective view of a device for training swimmers and performing physiotherapeutic exercises, in accordance with an example embodiment.

As shown on FIG. 2A, the device 200 comprises a cover 210 connected to the tank 205. The cover 210 may be configured to open completely or open partially, and may be removable, slidable, flippable, or any further type. The cover 210 may be configured as one part, or the cover may consist of several parts. The cover 210 is made of any suitable material. In some embodiments, the cover 210 is transparent or partially transparent. In FIG. 2A, the cover 210 of the device 200 is shown in a closed state. FIG. 2B shows the device 200 with the cover 220 in an open state. The cover 210 is configured to open to such an extent that the swimmer 120 can freely move in or move out the device 200.

Referring back to FIG. 2A, the swimmer 120 can be connected to the device 200 by a restraining element 215. The restraining element 215 has a first end and a second end. The restraining element 215 is connected on one end to the swimmer 120 via a harness 220, such as ankle harness, a leg harness, a thigh harness, a pelvis harness, a waist harness, a chest harness, a neck harness, a head harness, an arm harness, a shoulder harness, a wrist harness, and a body harness, and the like. A waist harness 220 is shown on FIG. 2A. The restraining element 215 may include a tether, a cord, a rope, a resilient member, such as a resin or a spring-loaded mechanical expander, and the like. Another end of the restraining element 215 is connected to one of the tank 205 and the cover 210 of the device 200. Thus, the restraining element 215 connected to the swimmer 120 allows the swimmer 120 to stay in a relatively stationary position during swimming. In such a way, in-place swimming may be enabled. When the swimmer 120, being connected to the device 200 by the restraining element 215, performs the swimming strokes, a resistance force occurs and the spine of the swimmer 120 stretches. The horizontal stretch of the spine of the swimmer allows the vertebrae to come to their natural position.

With continuing reference to FIG. 2A, another end of the restraining element 215 may be connected to the tank 205 or the cover through a unit 300 for measuring parameters of the swimmer. The unit 300 may be attached to the tank 205 or the cover 210 of the device 200. The unit 300 may be provided for measuring characteristics of the swimmer 120 during swimming and may be located on any side of the tank 205 or the cover 210 of the device 200. In an example embodiment, the unit 300 can be used for measuring parameters of the swimmer moving in any water reservoir. The water reservoir includes the device 200, a water tank, a pool, a bath, a surface water body, an indoor water park, an artificial water reservoir, and the like.

Figure 3:
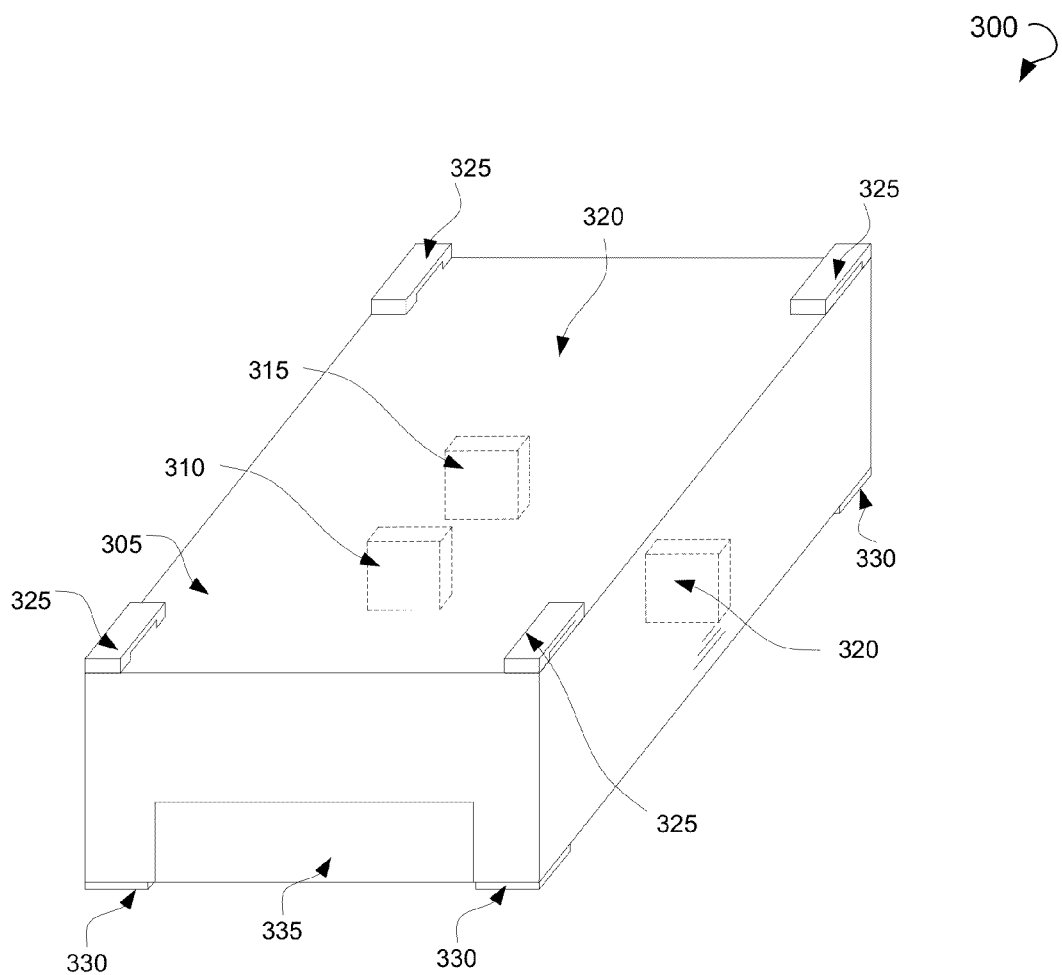
FIG. 3 is a schematic perspective view of a unit for measuring parameters of a swimmer, in accordance with an example embodiment.

FIG. 3 is a schematic perspective view of the unit 300 for measuring parameters of the swimmer. In an example embodiment, the unit 300 comprises a housing 305. The housing 305 may be of any suitable shape, such as rectangular, round, spherical, and the like. The housing 305 may be made of any suitable material, such as plastic, metal, ceramics, and the like. The unit 300 further comprises a motive force sensor 310 configured to measure a motive force associated with the swimmer. The motive force is generated by the swimmer moving in a water reservoir, such as a device for training swimmers and performing physiotherapeutic exercises as shown on FIG. 2A.

The unit 300 further comprises a processing unit 315. The processing unit 315 is configured to process measurements received from the motive force sensor 310. During the processing, processed measurements can be generated. The processing unit 315 is further configured to analyze the data received from the motive force sensor 310 in order to calculate parameters of the swimmer, such as a speed of the swimmer, a distance swam by the swimmer, intensity of movements of the swimmer, quantity of calories spent by the swimmer, and the like.

The unit 300 further comprises a transmitter 320. The transmitter 320 is configured to transmit the processed measurements to a peripheral unit (not shown). The peripheral unit includes a mobile telephone, a PC, a tablet PC, a laptop, a smartphone, a monitor, a communication unit of the device for training swimmers and performing physiotherapeutic exercises, and so forth. The transmitter 320 is configured to transmit data by wire or wirelessly using one or more of the following wireless protocols: Wi-Fi, Bluetooth, NFC, and so forth. The motive force sensor 310, the processing unit 315, and the transmitter 320 are enclosed in the housing 305.

The unit 300 further comprises one or more fasteners 325 connected to the housing 305. The fasteners 325 are configured to fasten a restraining element (not shown). In an example embodiment, the fasteners 325 are built in the housing 305, and the motive force sensor 310 is immovably fixed to the housing 305 so that deformations of fasteners 325, and, therefore, the housing 305, are transferred to the motive force sensor 310. In such a way, the restraining element is able to transfer the motive force from the swimmer to the motive force sensor 310. The motive force sensor 310 measures the motive force of the swimmer based on a tensile force acting on the motive force sensor 310 through the restraining element. In an example embodiment, the motive force sensor 310 includes one or more of a piezo sensor, a strain gauge, and any sensor able to measure the motive force of the swimmer.

In an example embodiment, the unit 300 is permanently attached to the water reservoir. In a further example embodiment, the unit 300 optionally comprises one or more fixing elements 330. The fixing elements 330 are disposed on the housing 305 and provided for attaching the unit 300 to the water reservoir.

Figure 4A:
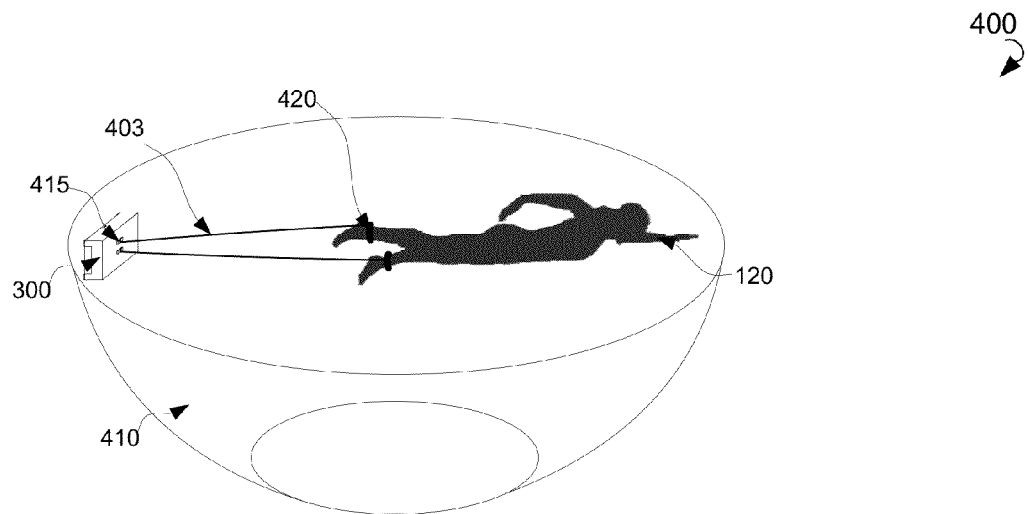
FIG. 4A is a view of attaching a unit for measuring parameters of a swimmer to a device for training swimmers and performing physiotherapeutic exercises, in accordance with an example embodiment.

FIG. 4A schematically shows a water reservoir 410 having the unit 300 attached to the water reservoir 410. The swimmer 120 is attached to the unit 300 of the water reservoir 410 by a restraining element 403. The first end of the restraining element 403 is connected to the unit 300 using fasteners 415. The second end of the restraining element 403 is connected to an ankle harness 420 on the swimmer 120.

Figure 4B:
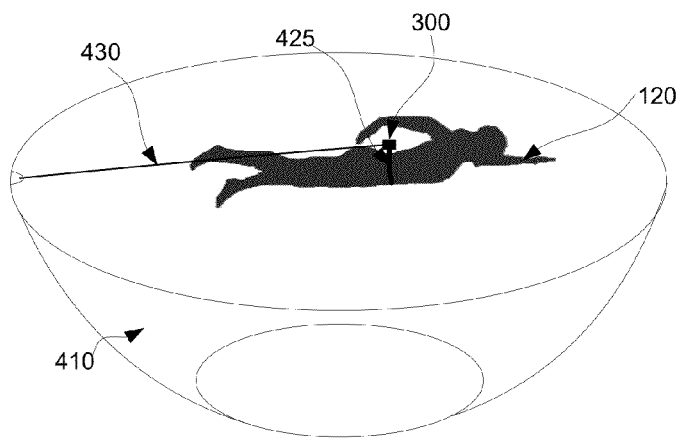
FIG. 4B is a view of attaching a unit for measuring parameters of a swimmer to a device for training swimmers and performing physiotherapeutic exercises, in accordance with an example embodiment.

In an example embodiment shown on FIG. 4B, the fixing elements (not shown) of the unit 300 are configured to be attached to the swimmer 120 (e.g., to a harness 425 worn by the swimmer 120). In such a case, the unit 300 is located on the swimmer 120, and the restraining element 430 connects the unit 300 with the water reservoir 410.

Figure 4C:
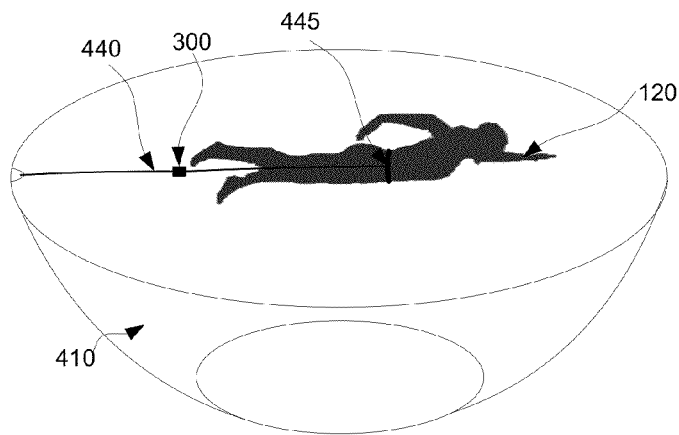
FIG. 4C is a view of attaching a unit for measuring parameters of a swimmer to a device for training swimmers and performing physiotherapeutic exercises, in accordance with an example embodiment.

In another example embodiment shown on FIG. 4C, the fixing elements (not shown) of the unit 300 are configured to be attached to a restraining element 440. In such a case, a first end of the restraining element 440 is connected to the swimmer 120 (e.g., using a waist harness 445). The unit 300 is disposed on the restraining element 440 (e.g., is attached to the middle of the restraining element 440 using the fixing elements). The second end of the restraining element 440 is connected to the water reservoir 410.

In an example embodiment, the unit 300 further comprises one or more of the following sensors (not shown): a sensor for measuring breathing rate, a sensor for measuring pulse, a sensor for measuring heart beats, a sensor for measuring degree of oxygen in blood, a sensor for measuring arterial blood pressure, a sensor for detecting position of the swimmer, a sensor for measuring frequency of movements of the swimmer, a sensor for measuring number of movements of the swimmer per time unit, and the like. Furthermore, the unit 300 comprises a power unit (not shown) configured to power the unit 300. The power unit includes a battery, a solar battery, an accumulator, and so forth. In an example embodiment, the housing 305 has a cavity (not shown) for accommodating the power unit. The cavity is closed with the closure 335.

Figure 5:
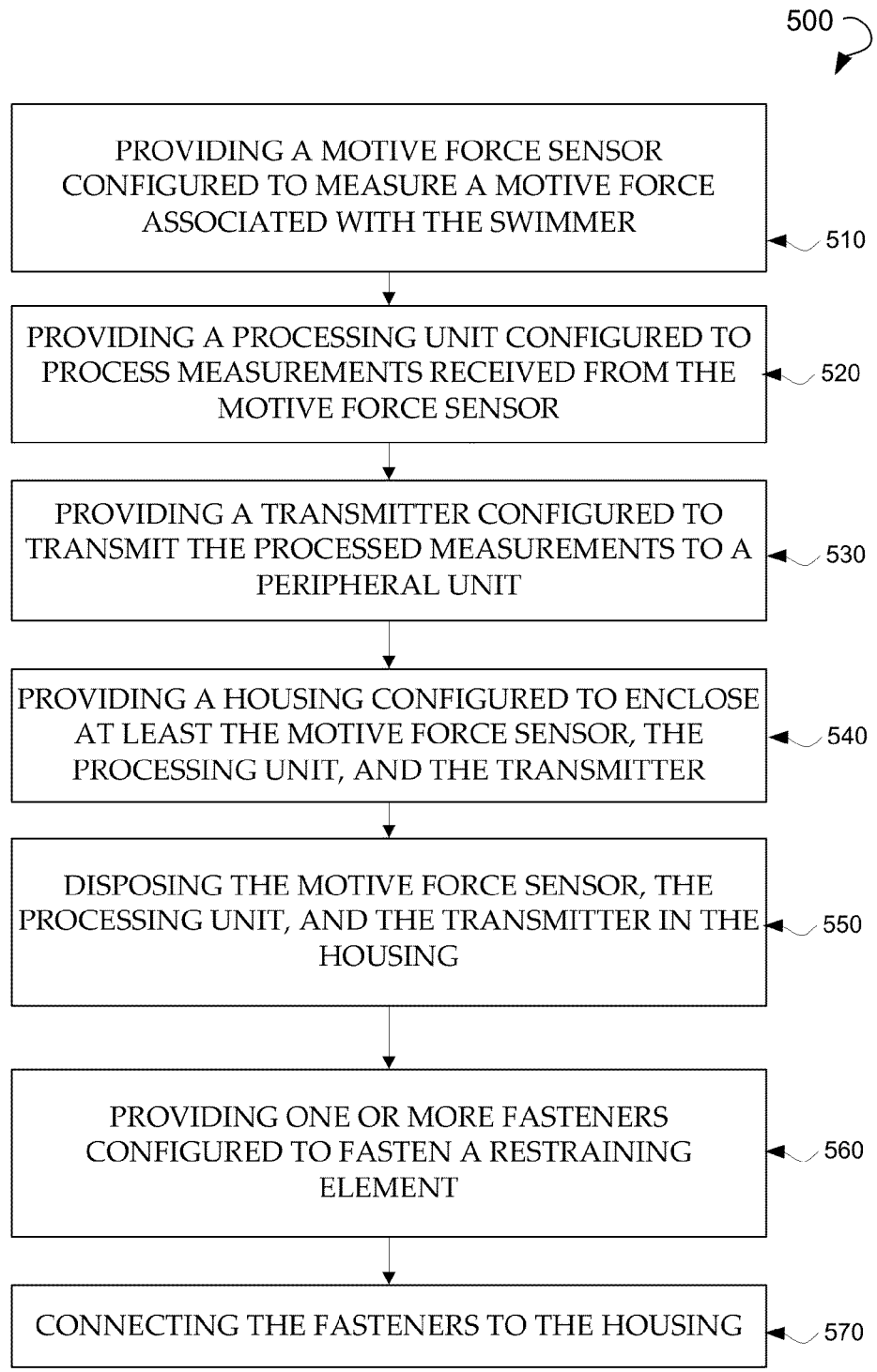
FIG. 5 is a flow chart illustrating a method for assembling a unit for measuring parameters of a swimmer, in accordance with an example embodiment.

FIG. 5 is a flow chart illustrating a method 500 for assembling a unit for measuring parameters of a swimmer, in accordance with an example embodiment. In the example shown, the method 500 commences with providing a motive force sensor at operation 510. The motive force sensor is configured to measure a motive force associated with the swimmer. The motive force is generated by the swimmer moving in a water reservoir. The water reservoir includes a water tank, a pool, a bath, a surface water body, an indoor water park, an artificial water reservoir, and so forth.

The method 500 continues with providing a processing unit at operation 520. The processing unit is configured to process measurements received from the motive force sensor. The processing generates processed measurements. The processing unit is further configured to analyze the data received from the motive force sensor. Based on the analyzed data, the processing unit is configured to calculate a speed of the swimmer, a distance swam by the swimmer, intensity of movements of the swimmer, quantity of calories spent by the swimmer, and the like.

The method 500 further comprises providing a transmitter at operation 530. The transmitter is configured to transmit the processed measurements to a peripheral unit. Furthermore, the transmitter is configured to transmit data by wire or wirelessly using one or more of the following wireless protocols: Wi-Fi, Bluetooth, and NFC. In an example embodiment, the peripheral unit includes a PC, a tablet PC, a laptop, a smartphone, a cell phone, a monitor, a personal digital device of the swimmer, and so forth.

The method 500 continues with providing a housing at operation 540. The housing is configured to enclose at least the motive force sensor, the processing unit, and the transmitter. At operation 550, the motive force sensor, the processing unit, and the transmitter are disposed in the housing. After disposing the elements of the motive force sensor, the processing unit, and the transmitter in the housing, one or more fasteners are provided at operation 560. The fasteners are configured to fasten a restraining element that transfers the motive force from the swimmer to the motive force sensor. At operation 570, the fasteners are connected to the housing.

The method 500 optionally comprises providing one or more of the following sensors: a sensor for measuring breathing rate, a sensor for measuring pulse, a sensor for measuring heart beats, a sensor for measuring degree of oxygen in blood, a sensor for measuring arterial blood pressure, a sensor for detecting position of the swimmer, a sensor for measuring frequency of movements of the swimmer, and a sensor for measuring number of movements of the swimmer per time unit. The sensors are attached to the housing. In an example embodiment, attaching to the housing includes disposing the sensors inside the housing.

The method 500 optionally comprises providing one or more fixing elements. The fixing elements are provided for attaching the unit for measuring parameters of a swimmer to the water reservoir, the restraining element, or the swimmer. The fixing elements are attached to the housing. In a further example embodiment, the method 500 optionally comprises providing a power unit and attaching the power unit to the housing. The power unit includes a battery, a solar battery, an accumulator, and so forth.

Referring back to FIG. 2A, the device 200 further comprises a communication unit (not shown). The communication unit is disposed inside the device 200 (i.e., is attached to the tank 205 or the cover 210). In an example embodiment, the communication unit is attached to an outer surface of the tank 205 or the cover 210. The communication unit may include a computer processing unit configured to collect, process, and store and transmit data received from the unit 300 for measuring parameters of the swimmer. The communication unit is configured to collect and store individual data of each swimmer 120. The communication unit collects the individual data by receiving the individual data of the swimmer from the unit 300. The communication unit selects a swimming mode based on the individual data of the swimmer and sets the swimming mode to the swimmer 120 in tank 205 of the device 200. In an example embodiment, the communication unit is configured to receive a swimmer's identity data. For example, the swimmer enters the identity data into the communication unit disposed on the device 200 or located inside the device 200. In an example embodiment, the swimmer enters the identity data into the communication unit or swipes a personal identity card. Based on the received swimmer identity data, the communication unit identifies the swimmer. By identifying the swimmer, the communication unit provides the swimmer with access to a personal profile of the swimmer. The communication unit is configured to receive swimmer preferences associated with a swimming mode. Furthermore, the communication unit sets a swimming mode for the swimmer according to the swimmer identity data and the swimmer preferences. The communication unit is further configured to transmit data by wire or wirelessly using one or more of the following wireless protocols: Wi-Fi, Bluetooth, NFC, and so forth.

As shown on FIG. 2A, the device 200 further comprises a display unit 225. The display unit 225 may include a monitor. The display unit 225 is located on any side of the device 200: on the bottom of the tank 205, on the cover 210, on the side walls of the tank 205 or the cover 210, and so forth. The display unit 225 is configured to display data received from the communication unit. The information includes parameters of the swimmer 120, such as speed of the swimmer, distance covered by the swimmer, and the amount of calories spent by the swimmer. In some embodiments, the display unit 225 displays the visualization of movements the swimmer 120 performs at the moment. Furthermore, in some embodiments, the display unit 225 displays the exercise to be done by the swimmer 120, such as a type of swimming, number of minutes of the exercise, the speed required for the exercise, and the like. The exercises are displayed on the display unit 225 one by one, so that the swimmer 120 may perform the complete training program. In some embodiments, the display unit 225 displays an instruction for the swimmer 120 to increase or decrease speed, to swim more intensively, and the like, so that the swimmer 120 can adhere to the training program. Furthermore, in some embodiments, the display unit 225 displays the conditions inside the device 200, such as air temperature, water temperature, air humidity, and the like.

In an example embodiment, the device 200 includes an illumination unit 230. The illumination unit 230 may include one or more lamps. The lamps are provided on any side of the cover 210 or the tank 205. In some embodiments, the light intensity is regulated in accordance with the preferences of the swimmer 120.

Figure 6A:
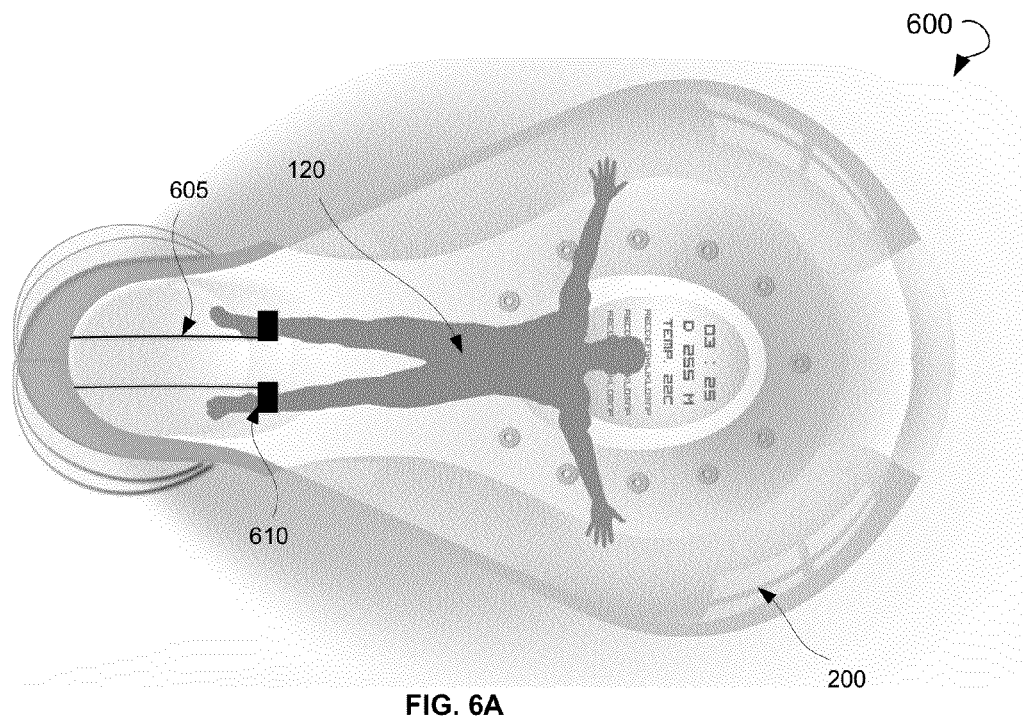
FIG. 6A shows a simplified top view of a device for training swimmers and performing physiotherapeutic exercises, in accordance with an example embodiment.

FIG. 6A is a top view 600 of another example embodiment of the device 200. According to this embodiment, the swimmer 120 is connected to the device 200 by the restraining element 605 connected by one end to the swimmer 120 via an ankle harness 610.

Figure 6B:
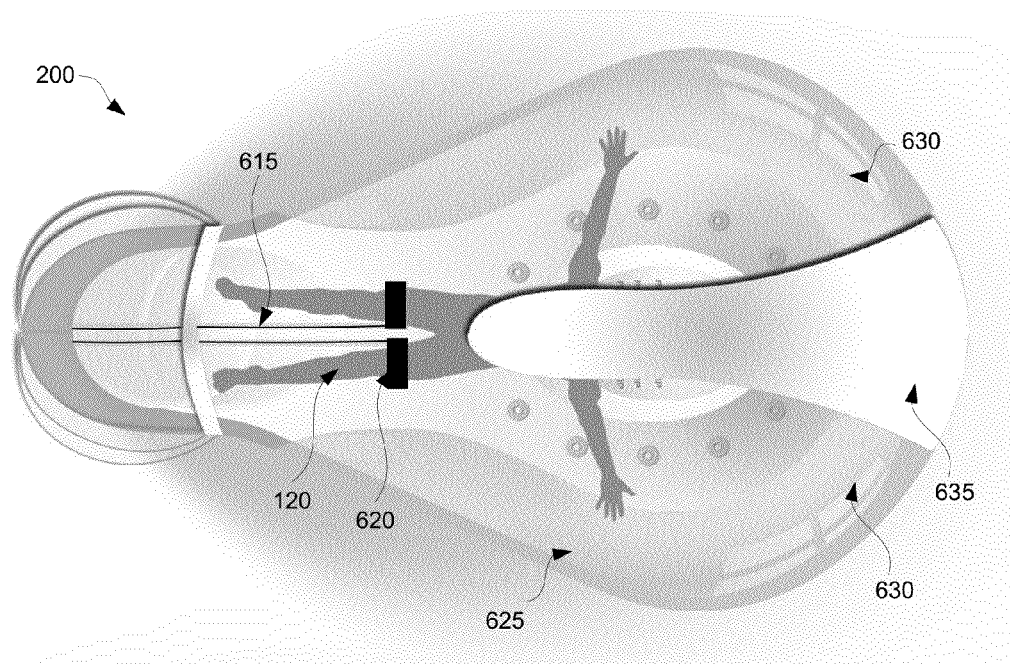
FIG. 6B shows a simplified top view of a device for training swimmers and performing physiotherapeutic exercises, in accordance with an example embodiment.

On FIG. 6B another example embodiment of the device 200 is shown. According to this embodiment, the swimmer 120 is connected to the device 200 by the restraining element 615 connected by one end to the swimmer 120 via a thigh harness 620. Furthermore, the device 200 shown on FIG. 2B comprises the cover 625 composed of several parts made of different materials: several transparent side parts 630 and a non-transparent part 635.

Figure 7:
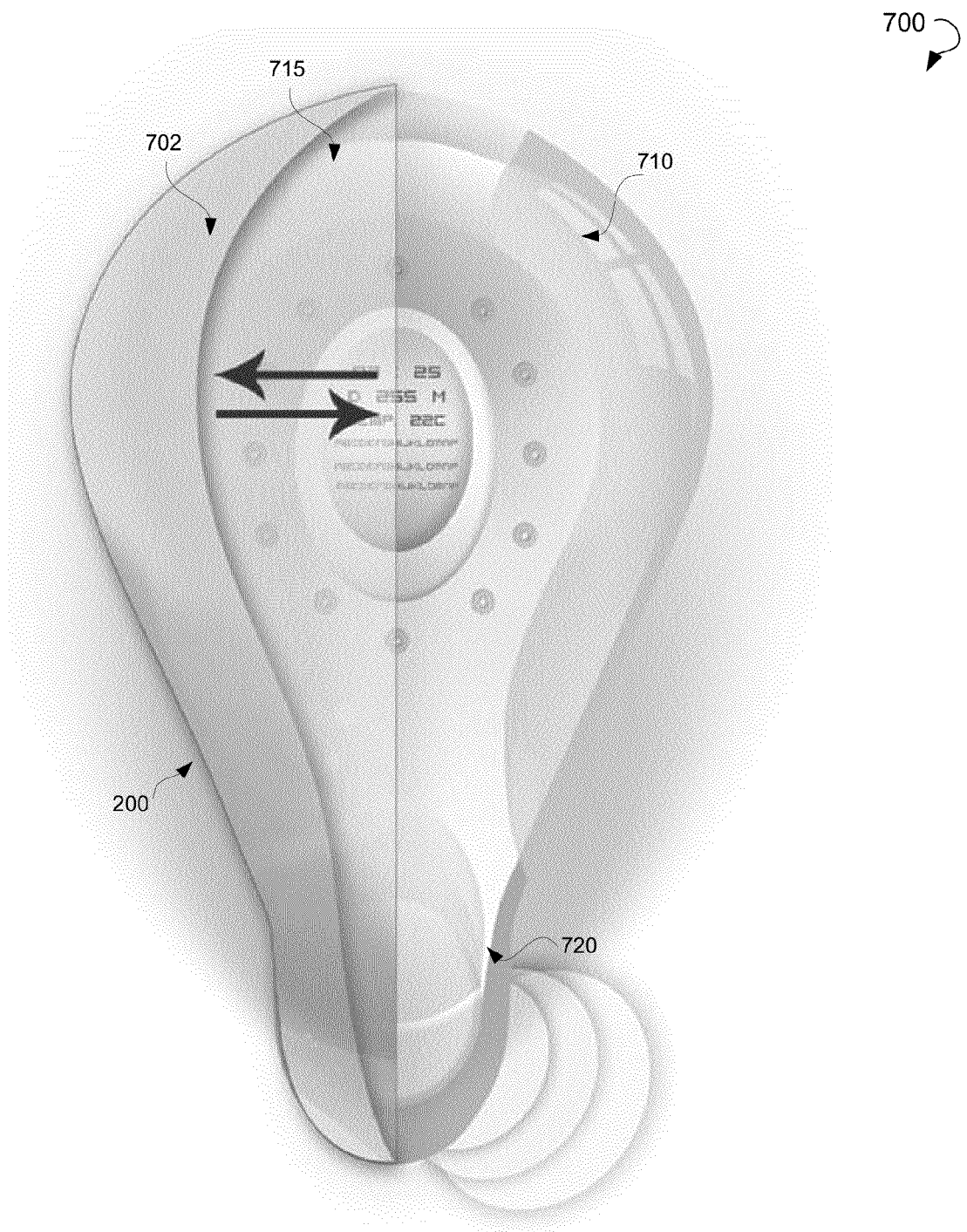
FIG. 7 shows a simplified top view of a device for training swimmers and performing physiotherapeutic exercises, in accordance with an example embodiment.

FIG. 7 shows a top view 700 of an example of the device 200, in accordance with a sample embodiment. The device 200 comprises a cover 702 that consists of two parts 710, 715 sliding down towards the tank 720 when opening. On FIG. 7, the part 715 is shown in a closed state, and the part 710 is shown in an open state.

Figure 8:
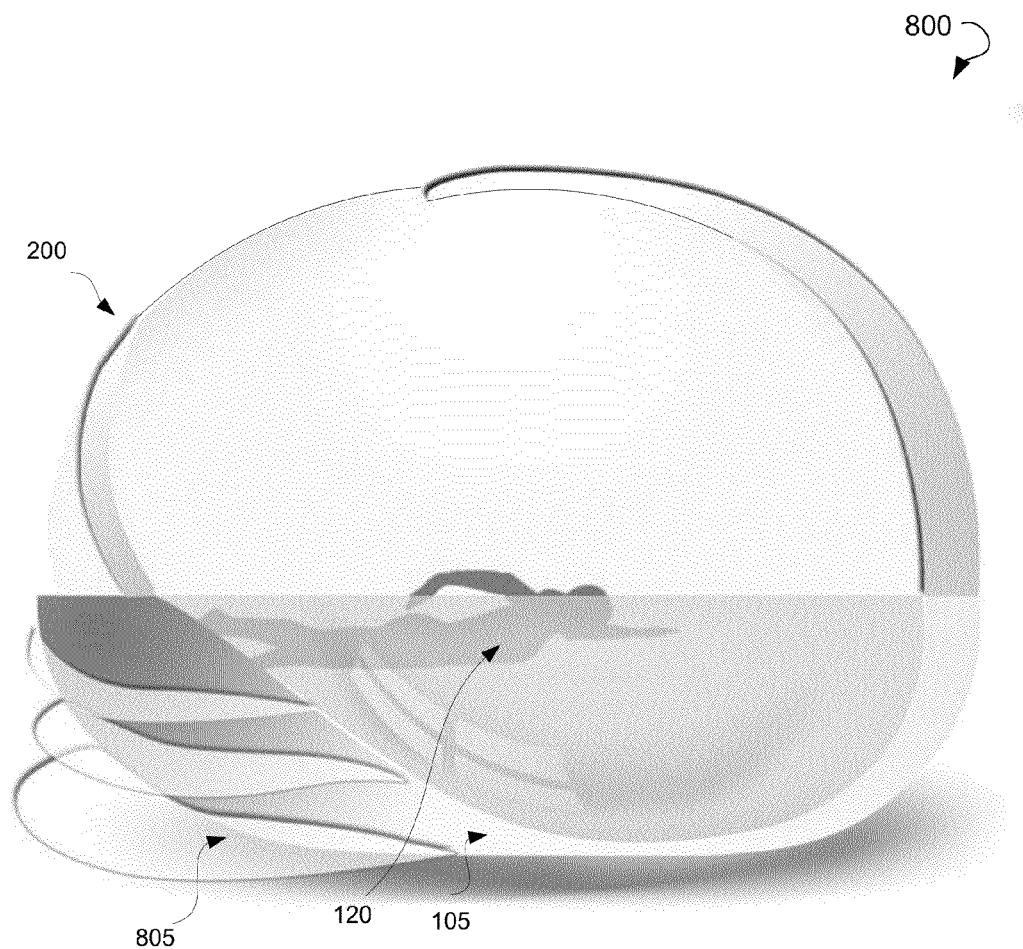
FIG. 8 shows a simplified side view of a device for training swimmers and performing physiotherapeutic exercises, in accordance with an example embodiment.

FIG. 8 is a side view 800 of an example of the device 200, in accordance with a sample embodiment. The device 200 is provided with a support 805 in order to make it easier for the swimmer 120 to enter and exit the device 200. The support 805 includes stairs, a sloping surface, and the like. In an example embodiment, the support 805 is covered with anti-slip material. The support 805 is located on any side of the tank 105. Furthermore, in a further example embodiment, the support 805 is circular and encircles the tank 105.

In some embodiments, the swimmer is monitored via a video recording unit, such as a video camera, and/or by a trainer or a doctor. The trainer or the doctor sees the visualization of the movements of the swimmer or the parameters of the swimmer collected by the unit for measuring parameters of the swimmer. Furthermore, the trainer or the doctor gives instructions to the swimmer, such as to change the parameters of their swimming, or to start or stop an exercise. The instructions are displayed for the swimmer on the monitor inside the device for training swimmers and performing physiotherapeutic exercises.

In some embodiments, the device for training swimmers and performing physiotherapeutic exercises comprises a microphone. In such an embodiment, the swimmer asks the trainer or the doctor questions, indicates how the swimmer feels at the moment, asks to change the mode of swimming, and the like.

In some embodiments, the swimmer is monitored via a communication unit without the presence of a person, such as a trainer or a doctor. In this embodiment, the communication unit analyzes the parameters of the swimmer, compares the parameters with the preset program of training, and gives instructions to the swimmer, such as to change the parameters of swimming, start another exercise, stop training, and the like.

In some embodiments, the device for training swimmers and performing physiotherapeutic exercises comprises a sound generating unit, such as speakers. In the case of such an embodiment, the swimmer hears the instructions via the speakers. The instructions include sound accompaniment, such as the voice of the trainer or the doctor, and the sound notices sent by the communication unit. In an example embodiment, the swimmer chooses music or a radio-channel that is reproduced via the speakers inside the device for training swimmers and performing physiotherapeutic exercises during training.

The device for training swimmer provides for completely satisfying all needs and preferences of the swimmer during training or rehabilitation. This is achieved due to the presence of the number of regulating units for controlling conditions inside the device for training swimmers and performing physiotherapeutic exercises (i.e., units that create a microclimate inside the device for training swimmers and performing physiotherapeutic exercises).

In an example embodiment, the regulating unit for controlling conditions includes an air conditioning unit. The air conditioning unit is configured to control air temperature, air relative humidity, air purity, speed of air movement, and so forth. In other words, the air conditioning unit helps to set and maintain the microclimate in the air space under the cover in accordance with the personal choice of the swimmer or in accordance with recommendations prescribed by the treatment or training program.

In another example embodiment, the regulating unit for controlling conditions includes a unit for saturating the air under the cover with fragrances and gas additives. The fragrances may include curative fragrances for therapy of respiratory organs, fragrances having a smell in accordance with the preferences of the swimmer, and so forth. The gas additives include oxygen, xenon, and the like. In some embodiments, the unit for saturating is used for saturation of water with gases, such as oxygen.

In some embodiments, the regulating unit for controlling conditions includes a temperature regulation unit that regulates the water temperature in the tank. The water temperature is set in accordance with recommendations prescribed by the treatment or training program or in accordance with the preference of the swimmer.

In some embodiments, the regulating unit for controlling conditions includes a water cleaning unit. The water cleaning unit includes a water filter. The water filter is switched on in pauses between trainings of the swimmers in the device for training swimmers and performing physiotherapeutic exercises. Alternatively, the water filter is switched on continuously.

In some embodiments, the regulating unit for controlling conditions includes a water salinity regulation unit. In such an embodiment, the water salinity regulation unit is used for adjusting the salinity of water inside the tank in accordance with the salinity of sea water. Furthermore, the swimmer may select the level of water salinity according to the preferences of the swimmer. In some example embodiments, the water cleaning unit and the water salinity regulation unit are implemented as a single unit.

In some embodiments, the regulating unit for controlling conditions includes a unit for creation of water jets and bubbles. The water jets and bubbles are used to massage the body of the swimmer.

In some embodiments, the device for training swimmers and performing physiotherapeutic exercises comprises a counter-current creation unit. The counter-current creation unit includes a turbine. The counter-current is used to provide an additional load to the swimmer in view of increasing the efforts exerted by the swimmer during swimming against the current.

Figure 9:
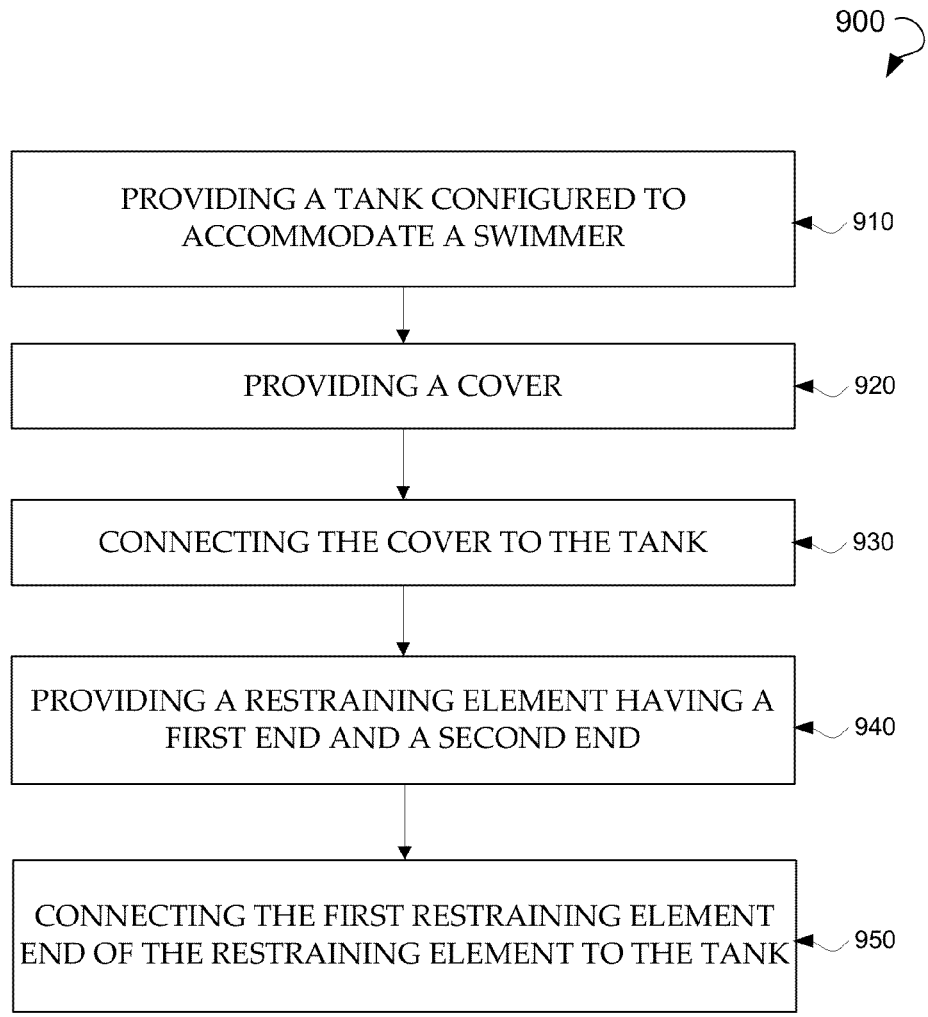
FIG. 9 is a flow chart illustrating a method for assembling a device for training swimmers and performing physiotherapeutic exercises, in accordance with an example embodiment.

FIG. 9 is a flow chart illustrating a method 900 for assembling a device for training swimmers and performing physiotherapeutic exercises, in accordance with an example embodiment. In the example shown, the method 900 commences with providing a tank at operation 910. The tank is configured to accommodate a swimmer. The method 900 further comprises providing a cover at operation 920. The cover is connected to the tank at operation 930. The method 900 continues with providing a restraining element at operation 940. The restraining element has a first end and a second end. The method 900 further comprises connecting the first end of the restraining element to the tank at operation 950. The second end of the restraining element is configured to be connected to the swimmer accommodated in the tank.

Optionally, the method 900 comprises providing a unit for measuring parameters of the swimmer. Providing of the unit for measuring parameters of the swimmer includes providing a motive force sensor, a processing unit, a transmitter, a housing, and one or more fasteners. The motive force sensor is configured to measure a motive force associated with the swimmer. The motive force is generated by the swimmer moving in the tank. The processing unit is configured to process measurements received from the motive force sensor. The processing generates processed measurements. The transmitter is configured to transmit the processed measurements to a peripheral unit. The housing is configured to enclose at least the motive force sensor, the processing unit, and the transmitter. The fasteners are connected to the housing and configured to fasten a restraining element. The restraining element transfers the motive force from the swimmer to the motive force sensor. The method 900 further comprises attaching the unit for measuring parameters of the swimmer to the tank or the cover.

In a further example embodiment, the method 900 optionally comprises providing a communication unit and attaching the communication unit to the tank or the cover. The communication unit is configured to collect, process, store, and transmit data received from the unit for measuring parameters of the swimmer. Furthermore, the method 900 optionally comprises providing one or more of the following: a display unit, a regulating unit for controlling conditions inside the device, a video recording unit, a microphone, a sound generating unit, an illumination unit, a counter-current creation unit, and so forth. The mentioned elements are attached to the tank and the cover.

Figure 10:
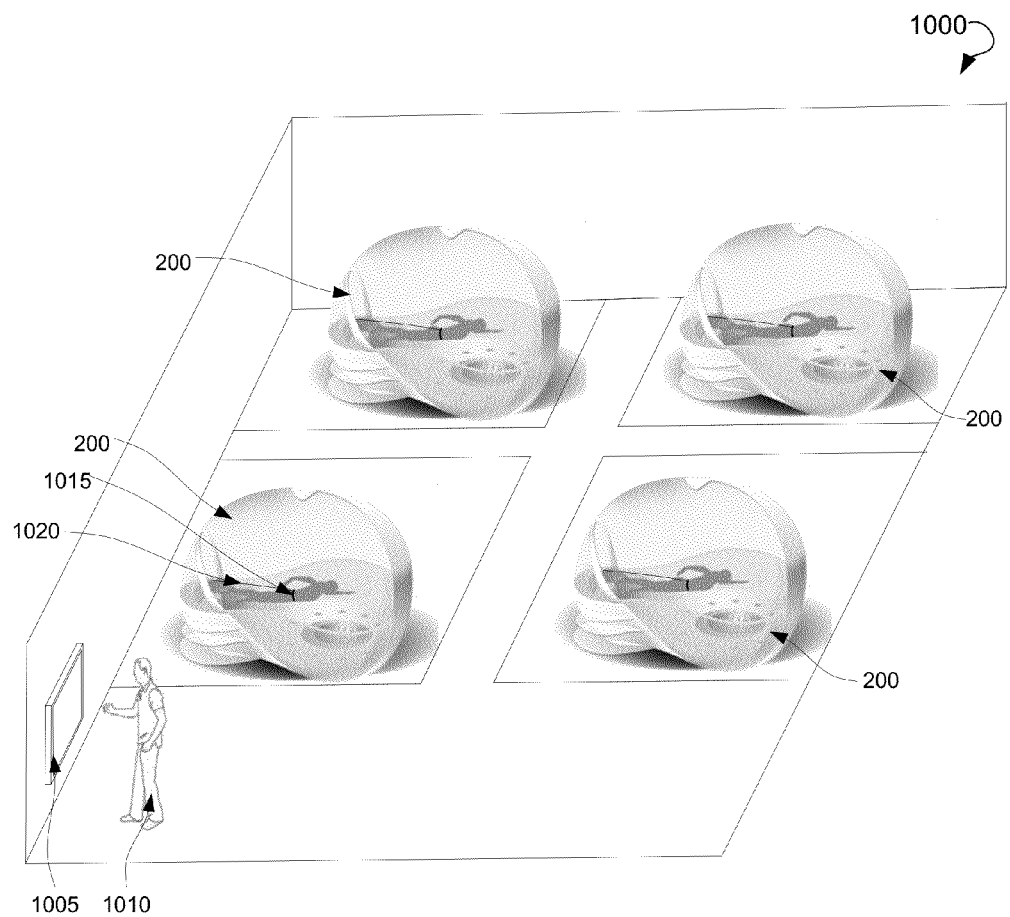
FIG. 10 is a simplified representation of a system of two or more devices for training swimmers and performing physiotherapeutic exercises, in accordance with an example embodiment.

FIG. 10 shows a scheme of a system 1000 of two or more devices 200 for training swimmers combined into a group, in accordance with an example embodiment. The described system 1000 of devices 200 for learning to swim, training swimmers, and performing physiotherapeutic exercises is capable of providing the swimmers with services without any assistance from staff in a place where the system is located, with automatic access to the devices for training swimmers and performing physiotherapeutic exercises and with remote monitoring and controlling of the training of the swimmer. The system 1000 of devices 200 may be located in a swimming center on the ground floor of an office building. For the group of devices 200, one communication unit 1005 is provided. The communication unit 1005 is capable of collecting and storing the individual data of each swimmer, automatically setting the modes for each swimmer in accordance with the stored personal data of each swimmer, maintaining the connection of the swimmer in each of the devices 200 with his personal trainer or doctor, synchronizing the operation of units for regulation of the conditions for each particular device 200, and the like. Thus, each device 200 is completely individualized for each swimmer. The communication unit 1005 includes a PC, a tablet PC, a monitor, a touch screen device, and like devices located in the swimming center.

The swimmer 1010 who wants to practice swimming visits the swimming center for the first time. An administrator (not shown) of the swimming center registers the swimmer 1010, and the swimmer 1010 may select a swimming program and conditions inside the device 200 suitable for the swimmer 1010. The information about the swimming program and conditions chosen by the swimmer 1005 is stored in a communication unit 1005. The swimmer 1010 is given a pass or an access code by the administrator. If necessary, the swimmer 1010 visits a doctor or a trainer for consultation as to which program is suitable for the swimmer 1010. Then the swimmer 1010 goes to the device 200 assigned to the swimmer 1010 by the communication unit 1005. The swimmer 1010 inputs the pass or the access code into the communication unit 1005. The information about the swimmer 1010 and the training program is already stored in the communication unit 1005. Therefore, after identification of the swimmer 1010, the communication unit 1005 sets the swimming program in accordance with the personal data of the swimmer 1010. Furthermore, the communication unit 1005 sets the conditions inside the device 200 assigned to the swimmer 1010 in accordance with the personal data of the swimmer 1010. Then the swimmer 1010 goes to the device 200 indicated by the communication unit 1005, puts on a harness 1015 connected to a restraining element 1020 on his waist or legs and enters the tank of the device 200. Once the swimmer 1010 is inside the tank, the cover of the device 200 may close, and the swimmer 1010 start training. The swimmer 1010 sees the exercises he should perform during training displayed on a display unit on the bottom of the tank of the device 200. If the swimmer 1010 performs the exercise incorrectly, a notice may be shown on the display unit (for example, to increase speed or intensity of swimming). In an example embodiment, the trainer or the doctor monitors the training of the swimmer 1010 online and gives instructions to the swimmer 1010. The swimmer 1010 may hear the voice of the trainer or the doctor inside the device 200, or the instructions may be shown on the display unit on the bottom of the tank of the device 200. When the time of the training is over, the swimmer 1010 sees the corresponding notice on the display unit, finishes training, removes the harness 1015, and exits the device 200.

In an example embodiment, the next time the swimmer 1010 comes, the swimmer 1010 needs only to input the pass or access code into the communication unit 1005, and the parameters of training and conditions are set automatically inside the device 200 in accordance with the stored personal data of the swimmer 1010. In case the swimmer 1010 needs additional consultation from the trainer or the doctor, the swimmer 1010 contacts the trainer or the doctor via the communication unit 1005 at any time during the training.

Furthermore, in order to avoid queues, in cases when the swimmer comes to have the training and all the devices for learning to swim, training swimmers, and performing physiotherapeutic exercises are unavailable, the swimmer may choose a time of training suitable for the swimmer. The chosen time is included in the personal data of the swimmer and stored in the communication unit, and one of the devices for learning to swim, training swimmers, and performing physiotherapeutic exercises is reserved for the swimmer at his specific time. Furthermore, in an example embodiment, the pass or the access code of the swimmer is configured not to allow the swimmer to have access to the device for learning to swim, training swimmers, and performing physiotherapeutic exercises at a time outside of his reserved time.

In the system 1000, a regulating unit for controlling conditions inside the device, such as an air conditioning unit, a unit saturating the air with fragrances and gas additives, a temperature regulation unit, a water cleaning unit, a water salinity regulation unit, and the like, is used to simultaneously regulate the conditions of the group of devices 200. Furthermore, the conditions set in each device 200 may be different. In other words, in case of the group of devices 200, the quantity of the regulating unit for controlling conditions inside the device may be optimized to provide economical advantage.

Thus, various systems and methods for training swimmers and for measuring parameters of a swimmer have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. A device for training swimmers and performing physiotherapeutic exercises comprising:
 a tank configured to accommodate a swimmer;
 a cover connected to the tank and configured to close the tank in such a way that the swimmer can remain within the tank which is enclosed with the cover, wherein the cover encloses the tank to maintain a microclimate inside the device, the microclimate including air conditions in an air space under the cover and water conditions in the tank;
 a restraining element having a first end and a second end, wherein the first end is connected to the cover, and the second end is configured to be connected to the swimmer; and
 a regulating unit configured to:
  receive instructions associated with the swimmer;
  based on the instructions, provide predetermined microclimate conditions within the tank enclosed with the cover;
  monitor parameters of the swimmer during a training of the swimmer;
  based on the parameters of the swimmer, determine preferential microclimate conditions; and
  based on the determination, provide the preferential microclimate conditions,
  wherein the microclimate is associated with the predetermined microclimate conditions and the preferential microclimate conditions, wherein the predetermined microclimate conditions and the preferential microclimate conditions are associated with at least an air temperature, a water temperature, a saturation of water with additives, and a saturation of air with additives.

2. The device of claim 1, further comprising a unit for measuring parameters of the swimmer, wherein the unit for measuring parameters of the swimmer includes:
 a motive force sensor configured to measure a motive force associated with the swimmer, wherein the motive force is generated by the swimmer moving in the tank;
 a processing unit configured to process measurements received from the motive force sensor, wherein the processing unit generates processed measurements;
 a transmitter configured to transmit the processed measurements to a peripheral unit;
 a housing configured to enclose at least the motive force sensor, the processing unit, and the transmitter; and
 one or more fasteners connected to the housing and configured to fasten the restraining element, wherein the restraining element is configured to transfer the motive force from the swimmer to the motive force sensor.

3. The device of claim 2, wherein the first end of the restraining element is connected to the cover through the unit for measuring parameters of the swimmer, wherein the unit for measuring parameters of the swimmer further includes one or more fixing elements for attaching to one or more of the tank, the cover, the restraining element, and the swimmer.

4. The device of claim 2, wherein the unit for measuring parameters of the swimmer further includes one or more of the following sensors: a sensor for measuring breathing rate, a sensor for measuring pulse, a sensor for measuring heart beats, a sensor for measuring degree of oxygen in blood, a sensor for measuring arterial blood pressure, a sensor for detecting position of the swimmer, a sensor for measuring frequency of movements of the swimmer, and a sensor for measuring number of movements of the swimmer per time unit.

5. The device of claim 1, wherein the restraining element includes one of a tether, a cord, a rope, and a resilient member.

6. The device of claim 1, wherein the second end of the restraining element is configured to be connected to the swimmer via one or more of an ankle harness, a leg harness, a thigh harness, a pelvis harness, a waist harness, a chest harness, a neck harness, a head harness, an arm harness, a shoulder harness, a wrist harness, and a body harness.

7. The device of claim 1, wherein the cover is configured to open completely or open partially.

8. The device of claim 1, wherein the cover includes one or more of the following: a removable cover, a sliding cover, and a flip cover.

9. The device of claim 1, further comprising a communication unit configured to collect, process, store, and transmit data received from the unit for measuring parameters of the swimmer.

10. The device of claim 9, wherein the communication unit is further configured to:
 collect and store individual data of the swimmer;
 select a swimming mode based on the individual data of the swimmer; and set the swimming mode for the swimmer in the tank, wherein the swimming mode relates to a swimming program, water conditions inside the tank, and atmospheric conditions inside the tank enclosed with the cover.

11. The device of claim 9, wherein the communication unit is further configured to:
receive swimmer identity data;
automatically identify the swimmer based on the received swimmer identity data;
receive swimmer preferences associated with a swimming mode; and
set a swimming mode for the swimmer, wherein the swimming mode is set according to the swimmer identity data and the swimmer preferences, wherein the swimming mode is further associated with a swimming program, water conditions inside the tank, and atmospheric conditions inside the tank enclosed with the cover.

12. The device of claim 9, wherein the communication unit is further configured to:
transmit data by wire or wirelessly using one or more of the following wireless protocols: Wi-Fi, Bluetooth, and Near Field Communication.

13. The device of claim 1, further comprising a display unit configured to display one or more of the following: data received from the communication unit, visualization of movements of the swimmer, an exercise to be done by the swimmer, an instruction for the swimmer, and conditions inside the device.

14. The device of claim 1, further comprising a video camera, a microphone, a sound generating unit, and an illumination unit.

15. The device of claim 1, comprising a unit for saturating air or water with fragrances, a temperature regulation unit, and a water cleaning unit, wherein further optionally comprising a water salinity regulation unit or a unit for creation of water jets.

16. A method for assembling a device for training swimmers and performing physiotherapeutic exercises, the method comprising:
providing a tank configured to accommodate a swimmer;
providing a cover;
connecting the cover to the tank, wherein the cover is configured to close the tank in such a way the swimmer can remain within the tank which is enclosed with the cover, wherein the cover encloses the tank to maintain a microclimate inside the device, the microclimate including air conditions in an air space under the cover and water conditions in the tank;
providing a restraining element wherein the restraining element has a first end and a second end;
providing a regulating unit attached to one or more of the tank and the cover for:
receiving instructions associated with the swimmer;
based on the instructions, providing predetermined microclimate conditions within the tank enclosed with the cover;
monitoring parameters of the swimmer during a training of the swimmer;
based on the parameters of the swimmer, determining preferential microclimate conditions; and
based on the determination, providing the preferential microclimate conditions,
wherein the microclimate is associated with the predetermined microclimate conditions and the preferential microclimate conditions, wherein the predetermined microclimate conditions and the preferential microclimate conditions are associated with at least an air temperature, a water temperature, a saturation of water with additives, and a saturation of air with additives; and
connecting the first end of the restraining element to the cover, wherein the second end of the restraining element is configured to be connected to the swimmer.

17. The method of claim 16, further comprising:
providing a unit for measuring parameters of the swimmer, wherein the providing of the unit for measuring parameters of the swimmer includes:
providing a motive force sensor configured to measure a motive force associated with the swimmer, wherein the motive force is generated by the swimmer moving in the tank;
providing a processing unit configured to process measurements received from the motive force sensor, wherein the processing generates processed measurements;
providing a transmitter configured to transmit the processed measurements to a peripheral unit;
providing a housing configured to enclose at least the motive force sensor, the processing unit, and the transmitter; and
providing one or more fasteners connected to the housing and configured to fasten a restraining element, wherein the restraining element is configured to transfer the motive force from the swimmer to the motive force sensor; and
attaching the unit for measuring parameters of the swimmer to the tank or the cover.

18. The method of claim 16, further comprising:
providing a communication unit, wherein the communication unit is configured to collect, process, store, and transmit data received from the unit for measuring parameters of the swimmer; and
attaching the communication unit to the tank or the cover.

19. The method of claim 16, further comprising:
providing one or more of the following: a display unit, a video recording unit, a microphone, a sound generating unit, an illumination unit, and a counter-current creation unit; and
attaching one or more of the display unit, the video recording unit, the microphone, the sound generating unit, the illumination unit, and the counter-current creation unit to one or more of the tank and the cover.

20. A device for learning to swim, training swimmers, and performing physiotherapeutic exercises, the device comprising:
a tank configured to accommodate a swimmer;
a cover connected to the tank and configured to close the tank in such a way that the swimmer can remain within the tank which is enclosed with the cover, wherein the cover encloses the tank to maintain a microclimate inside the device, the microclimate including air conditions in an air space under the cover and water conditions in the tank;
a regulating unit configured to:
receive instructions associated with the swimmer;
based on the instructions, provide predetermined microclimate conditions within the tank enclosed with the cover;
monitor parameters of the swimmer during a training of the swimmer;
based on the parameters of the swimmer, determine preferential microclimate conditions; and based on the determination, provide the preferential microclimate conditions, wherein the microclimate is associated with the predetermined microclimate conditions and the preferential microclimate conditions, wherein the predetermined microclimate conditions and the preferential microclimate conditions are associated with at least an air temperature, a water temperature, a saturation of water with additives, and a saturation of air with additives;

wherein the regulating unit includes one or more of the following: a unit for saturating air and water with fragrances, a temperature regulation unit, a water cleaning unit, a water salinity regulation unit, and a unit for creation of water jets and bubbles;

a restraining element having a first end and a second end, wherein the first end is connected to the cover and the second end is configured to be connected to the swimmer;

a unit for measuring parameters of the swimmer, wherein the unit for measuring parameters of the swimmer includes:

a motive force sensor configured to measure a motive force associated with the swimmer, wherein the motive force is generated by the swimmer moving in the tank;

a processing unit configured to process measurements received from the motive force sensor, wherein the processing generates processed measurements;

a transmitter configured to transmit the processed measurements to a peripheral unit;

a housing configured to enclose at least the motive force sensor, the processing unit, and the transmitter; and one or more fasteners connected to the housing and configured to fasten a restraining element, wherein the restraining element is configured to transfer the motive force from the swimmer to the motive force sensor;

one or more fixing elements for attaching to one or more of the tank, the cover, the restraining element, and the swimmer;

one or more of the following sensors: a sensor for measuring breathing rate, a sensor for measuring pulse, a sensor for measuring heart beats, a sensor for measuring degree of oxygen in blood, a sensor for measuring arterial blood pressure, a sensor for detecting position of the swimmer, a sensor for measuring frequency of movements of the swimmer, and a sensor for measuring number of movements of the swimmer per time unit;

a communication unit configured to:
    collect, process, store, and transmit data received from the unit for measuring parameters of the swimmer;
    collect and store individual data of the swimmer;
    select a swimming mode based on the individual data of the swimmer;
    set the swimming mode for the swimmer in the tank;
    receive swimmer identity data;
    identify the swimmer based on the received swimmer identity data;
    receive swimmer preferences associated with a swimming mode; and
    set a swimming mode for the swimmer, wherein the swimming mode is set according to the swimmer identity data and the swimmer preferences; and
    transmit data by wire or wirelessly using one or more of the following wireless protocols: Wi-Fi, Bluetooth, and Near Field Communication;

a display unit configured to display one or more of the following: data received from the communication unit, visualization of movements of the swimmer, an exercise to be done by the swimmer, an instruction for the swimmer, and conditions inside the device, wherein the display unit is secured to a bottom of the tank or to the cover, and the display unit is substantially parallel to the bottom of the tank; and one or more of the following: a video recording unit, a microphone, a sound generating unit, an illumination unit, and a counter-current creation unit.

21. The device of claim 2, wherein the first end of the restraining element is directly connected to the cover, and wherein the unit for measuring parameters is operatively attached to the restraining element between the first end and the second end.

22. The device of claim 13, wherein the display unit is secured to a bottom of the tank, and the display is substantially parallel to the bottom of the tank.

23. The device of claim 1, further comprising a water salinity regulation unit.

24. The device of claim 1, further comprising a video recording unit configured to capture images of the swimmer accommodated within the tank which is enclosed with the cover.

* * * * *